United States Patent
Martinek et al.

(10) Patent No.: US 8,133,231 B2
(45) Date of Patent: Mar. 13, 2012

(54) INSTRUMENT KIT AND METHOD FOR PERFORMING MENISCAL REPAIR

(75) Inventors: Jonathan Martinek, Cheshire, CT (US); Stephen W. Zlock, Redding, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 295 days.

(21) Appl. No.: 12/613,967

(22) Filed: Nov. 6, 2009

(65) Prior Publication Data

US 2010/0094363 A1    Apr. 15, 2010

Related U.S. Application Data

(62) Division of application No. 10/774,828, filed on Jul. 6, 2004, now Pat. No. 7,632,284.

(51) Int. Cl.
A61B 17/58    (2006.01)
A61B 17/60    (2006.01)
A61F 2/00    (2006.01)

(52) U.S. Cl. .......................... 606/88; 606/86 R

(58) Field of Classification Search ............... 606/86 R, 606/88, 96, 99
See application file for complete search history.

(56) References Cited

U.S. PATENT DOCUMENTS

| | | | |
|---|---|---|---|
| 3,093,134 A | 6/1963 | Roehr | |
| 3,842,824 A | 10/1974 | Neufeld | |
| 4,055,172 A | 10/1977 | Ender et al. | |
| 4,169,470 A | 10/1979 | Ender et al. | |
| 4,580,563 A | 4/1986 | Gross | |
| 4,635,637 A | 1/1987 | Schreiber | |
| 4,657,002 A | 4/1987 | Ray | |
| 4,686,972 A | 8/1987 | Kurland | |
| 4,686,978 A | 8/1987 | Wadsworth | |
| 4,736,738 A | 4/1988 | Lipovsek et al. | |
| 4,791,919 A | 12/1988 | Eloy et al. | |
| 4,834,081 A | 5/1989 | Van Zile | |
| 4,917,100 A | 4/1990 | Nottke | |
| 4,932,962 A | 6/1990 | Yoon et al. | |
| 4,944,744 A | 7/1990 | Ray | |
| 4,950,271 A | 8/1990 | Lewis et al. | |
| 4,995,875 A | 2/1991 | Coes | |
| 5,002,562 A | 3/1991 | Oberlander | |
| 5,013,314 A | 5/1991 | Firica et al. | |
| 5,019,083 A | 5/1991 | Klapper et al. | |
| 5,035,697 A | 7/1991 | Frigg | |
| 5,037,422 A | 8/1991 | Hayhurst et al. | |
| 5,045,054 A | 9/1991 | Hood et al. | |
| 5,059,196 A | 10/1991 | Coates | |
| 5,059,206 A | 10/1991 | Winters | |
| 5,061,271 A | 10/1991 | Van Zile | |
| 5,062,843 A | 11/1991 | Mahony, III | |
| 5,064,427 A | 11/1991 | Burkinshaw | |
| 5,071,420 A | 12/1991 | Paulos | |
| 5,078,718 A | 1/1992 | Moll et al. | |
| 5,100,417 A | 3/1992 | Cerier et al. | |

(Continued)

*Primary Examiner* — Thomas C. Barrett
*Assistant Examiner* — Christine Nelson

(57) ABSTRACT

An instrument kit for performing a repair procedure on a meniscal tear in a knee for use in combination with a mechanical repair device is disclosed. The instrument kit includes at least one template including an elongate body defining X, Y and Z axes. The elongate body adapted for insertion in a knee of the patient to approximate a path to a meniscal tear within the knee. The elongate body has a length defining the X-axis. The instrument kit including a first template having a linear elongate body, a second template having a distal end portion which is offset in a direction of the Y-axis, and a third template having a distal end portion which is offset in a direction of the Z-axis.

5 Claims, 10 Drawing Sheets

U.S. PATENT DOCUMENTS

| | | |
|---|---|---|
| 5,102,421 A | 4/1992 | Anspach, Jr. |
| 5,114,065 A | 5/1992 | Storace |
| 5,141,520 A | 8/1992 | Goble et al. |
| 5,152,749 A | 10/1992 | Giesy et al. |
| 5,152,765 A | 10/1992 | Ross et al. |
| 5,152,792 A | 10/1992 | Watkins et al. |
| 5,154,189 A | 10/1992 | Oberlander |
| 5,161,725 A | 11/1992 | Murray et al. |
| 5,167,619 A | 12/1992 | Wuchinich |
| 5,171,240 A | 12/1992 | Hanwong |
| 5,176,683 A | 1/1993 | Kimsey et al. |
| 5,190,551 A | 3/1993 | Chin et al. |
| 5,192,283 A | 3/1993 | Ling et al. |
| 5,192,288 A | 3/1993 | Thompson et al. |
| 5,203,784 A | 4/1993 | Ross et al. |
| 5,213,112 A | 5/1993 | Niwa et al. |
| 5,217,463 A | 6/1993 | Mikhail |
| 5,220,928 A | 6/1993 | Oddsen et al. |
| 5,222,958 A | 6/1993 | Chin |
| 5,224,946 A | 7/1993 | Hayhurst et al. |
| 5,236,431 A | 8/1993 | Gogolewski et al. |
| 5,250,055 A | 10/1993 | Moore et al. |
| 5,257,713 A | 11/1993 | Green et al. |
| 5,258,010 A | 11/1993 | Green et al. |
| 5,258,016 A | 11/1993 | DiPoto et al. |
| 5,261,914 A | 11/1993 | Warren |
| 5,282,804 A | 2/1994 | Salyer |
| 5,284,484 A | 2/1994 | Hood et al. |
| 5,285,010 A | 2/1994 | Huber |
| 5,290,290 A | 3/1994 | Mikhail |
| 5,290,291 A | 3/1994 | Linden |
| 5,290,300 A | 3/1994 | Cosgrove et al. |
| 5,300,077 A | 4/1994 | Howell |
| 5,303,694 A | 4/1994 | Mikhail |
| 5,308,349 A | 5/1994 | Mikhail |
| 5,308,350 A | 5/1994 | Mikhail |
| 5,318,570 A | 6/1994 | Hood et al. |
| 5,320,625 A | 6/1994 | Bertin |
| 5,320,626 A | 6/1994 | Schmieding |
| 5,324,297 A | 6/1994 | Hood et al. |
| 5,328,077 A | 7/1994 | Lou |
| 5,330,481 A | 7/1994 | Hood et al. |
| 5,334,194 A | 8/1994 | Mikhail |
| 5,364,400 A | 11/1994 | Rego, Jr. et al. |
| 5,370,662 A | 12/1994 | Stone et al. |
| 5,374,268 A | 12/1994 | Sander |
| 5,376,093 A | 12/1994 | Newman |
| 5,380,331 A | 1/1995 | Mikhail |
| 5,382,251 A | 1/1995 | Hood et al. |
| 5,397,330 A | 3/1995 | Mikhail |
| 5,417,693 A | 5/1995 | Sowden et al. |
| 5,423,471 A | 6/1995 | Mastri et al. |
| 5,431,651 A | 7/1995 | Goble |
| 5,439,467 A | 8/1995 | Benderev et al. |
| 5,456,686 A | 10/1995 | Klapper et al. |
| 5,467,786 A | 11/1995 | Allen et al. |
| 5,470,336 A | 11/1995 | Ling et al. |
| 5,476,466 A | 12/1995 | Barrette et al. |
| 5,501,692 A | 3/1996 | Riza |
| 5,520,693 A | 5/1996 | McGuire et al. |
| 5,549,612 A | 8/1996 | Yapp et al. |
| 5,554,154 A | 9/1996 | Rosenberg |
| 5,562,736 A | 10/1996 | Ray et al. |
| 5,569,262 A | 10/1996 | Carney |
| 5,603,716 A | 2/1997 | Morgan et al. |
| 5,624,446 A | 4/1997 | Harryman, II |
| 5,630,819 A | 5/1997 | Ashby et al. |
| 5,635,637 A | 6/1997 | Boult et al. |
| 5,662,657 A | 9/1997 | Carn |
| 5,681,318 A | 10/1997 | Pennig et al. |
| 5,683,469 A | 11/1997 | Johnson et al. |
| 5,702,462 A | 12/1997 | Oberlander |
| 5,702,463 A | 12/1997 | Pothier et al. |
| 5,713,906 A | 2/1998 | Grothues-Spork et al. |
| 5,722,978 A | 3/1998 | Jenkins, Jr. |
| 5,732,992 A | 3/1998 | Mauldin |
| 5,733,292 A | 3/1998 | Gustilo |
| 5,743,909 A | 4/1998 | Collette |
| 5,785,714 A | 7/1998 | Morgan et al. |
| 5,788,701 A | 8/1998 | McCue |
| 5,800,546 A | 9/1998 | Marik et al. |
| 5,830,220 A | 11/1998 | Wan et al. |
| 5,842,477 A | 12/1998 | Naughton et al. |
| 5,885,291 A | 3/1999 | Moskovitz et al. |
| 5,885,299 A | 3/1999 | Winslow et al. |
| 5,899,907 A | 5/1999 | Johnson |
| 5,902,339 A | 5/1999 | Keller |
| 5,904,692 A | 5/1999 | Steckel et al. |
| 5,910,148 A | 6/1999 | Reimels et al. |
| 5,918,604 A | 7/1999 | Whelan |
| 5,928,252 A | 7/1999 | Steadman et al. |
| 5,951,559 A | 9/1999 | Burkhart |
| 5,951,564 A | 9/1999 | Schroder et al. |
| 5,954,747 A | 9/1999 | Clark |
| 5,968,050 A | 10/1999 | Torrie |
| 5,980,573 A | 11/1999 | Shaffner |
| 5,997,552 A | 12/1999 | Person et al. |
| 5,997,554 A | 12/1999 | Thompson |
| 6,004,326 A | 12/1999 | Castro et al. |
| 6,015,408 A | 1/2000 | Pichon et al. |
| 6,022,356 A | 2/2000 | Noyes et al. |
| 6,042,572 A | 3/2000 | Fowler |
| 6,045,555 A | 4/2000 | Smith et al. |
| 6,056,778 A | 5/2000 | Grafton et al. |
| 6,063,091 A | 5/2000 | Lombardo et al. |
| 6,083,225 A | 7/2000 | Winslow et al. |
| 6,132,433 A | 10/2000 | Whelan |
| 6,146,385 A | 11/2000 | Torrie et al. |
| 6,187,012 B1 | 2/2001 | Masini |
| 6,190,392 B1 | 2/2001 | Vandewalle et al. |
| 6,203,572 B1 | 3/2001 | Johnson et al. |
| 6,238,435 B1 | 5/2001 | Meulink et al. |
| 6,245,111 B1 | 6/2001 | Shaffner |
| 6,267,767 B1 | 7/2001 | Strobel et al. |
| 6,270,502 B1 | 8/2001 | Stulberg |
| 6,273,892 B1 | 8/2001 | Orbay et al. |
| 6,277,123 B1 | 8/2001 | Maroney et al. |
| 6,352,538 B2 | 3/2002 | McGuire et al. |
| 6,358,253 B1 | 3/2002 | Torrie et al. |
| 6,371,124 B1 | 4/2002 | Whelan |
| 6,375,658 B1 | 4/2002 | Hangody et al. |
| 6,613,054 B2 | 9/2003 | Scribner et al. |
| 6,666,872 B2 | 12/2003 | Barreiro et al. |
| 7,048,682 B2 | 5/2006 | Neisz et al. |
| 7,153,307 B2 | 12/2006 | Scribner et al. |
| 2002/0002374 A1* | 1/2002 | Barreiro et al. .............. 606/142 |
| 2002/0151975 A1* | 10/2002 | Farr et al. .................. 623/14.12 |
| 2004/0267270 A1* | 12/2004 | Jacobs et al. .................. 606/86 |
| 2004/0267276 A1* | 12/2004 | Camino et al. .................. 606/99 |

* cited by examiner

INSTRUMENT KIT AND METHOD FOR PERFORMING MENISCAL REPAIR

CROSS-REFERENCE TO RELATED APPLICATIONS

This application is a Divisional application claiming the benefit of and priority to U.S. application Ser. No. 10/774,828, filed on Jul. 6, 2004, now U.S. Pat. No. 7,632,284, the entire disclosure of which is incorporated herein by reference.

BACKGROUND

1. Technical Field

The present disclosure relates generally to the field of endoscopic surgical devices and, more particularly, to an instrument kit and method for performing a meniscal repair procedure.

2. Background of Related Art

Intracorporeal tearing of body tissue occurs most often at bone joint regions. Certain body tissues act as a cushion for absorbing the forces of joint movement, preventing friction in the joint and channeling the mechanical stress and strain associated with such movement. Like any shock-absorbing material, such body tissues experience failure when applied forces exceed the strength of the material, including failure as a result of shear and tension forces.

Human joints include a type of shock-absorbing body tissue known as a "meniscus" made up of a fibrous cartilage. For example, each human knee includes two generally crescent-shaped menisci residing on the tibial plateau, commonly known in the medical community as the medial meniscus and the lateral meniscus. The peripheral rim of the meniscus is thick, tapering down to a thin free inner border. The superior surface is concave in order to contact the femoral condyles, while the inferior surface is planar to contact the tibial plateau. It is generally recognized that repair of meniscal lesions and/or tears, to the extent possible, is preferable to excision so as to attempt to maintain the normality of the meniscus and have it continue to function properly.

Untreated meniscal tears may result in ultimate deterioration of the meniscus as well as other complications. Generally, repair of a meniscal tear is accomplished by holding the sides of the tear together, usually for at least six weeks, to allow the body to regenerate. Accordingly, several different techniques have been developed for repairing meniscal tears.

Many of the presently known techniques for repairing meniscal tears in the knee have proven to be a significant benefit in the relief of knee injuries, pain and discomfort. Four major techniques are known in the field of meniscal repair, namely, "open" technique, "inside-out" technique, "outside-in" technique and "all inside" technique. Each of these techniques generally involves the suturing of the sides of the meniscal tear together.

One known technique for repairing torn meniscus tissue involves the use of a pair of surgical needles which are inserted through cannuli into the knee on opposite sides of the meniscal tear. The ends of the needles include a length of suture material which is pushed down through the cannuli and across the tear. An incision is made in the skin at the point where the needle exits the knee joint so that the leading end of each needle may be grasped and pulled through the joint. The ends of the suture are then grasped after the needles are removed from the suture ends and the suture is then tied so that a horizontal suture is created in the meniscus. This procedure is repeated for placement of as many sutures as necessary to repair the meniscal tear. As is apparent, this procedure is both time consuming and difficult to effect.

Another procedure is outlined in U.S. Pat. No. 5,002,562. Briefly, in this procedure, a barbed clip and an instrument for applying the clip are utilized. The instrument includes a pair of opposed arcuate jaws which are shaped to hold a complementary shaped curved surgical clip therebetween. The barbs of the clip are retained within notches in the jaws until the clip is inserted. The legs of the clip are joined by a flexible suture material. The jaws are biased in a normally open position, and as the jaws are pushed into the tissue, the jaws are closed to overlap thereby moving the legs of the clip together. The jaws are then reopened and backed out of the tissue leaving the clip in position in the tissue.

Another technique and apparatus for meniscal repair is illustrated in U.S. Pat. No. 5,997,552. The '552 patent details a meniscal fastener applying device which applies fasteners sequentially from a longitudinally extending magazine. An advancing mechanism is operatively associated with an elongated body portion of the device for sequentially advancing surgical fasteners from a fastener supply to a firing position in alignment with a firing mechanism. The fastener includes a pair of anchor members whose proximal-most ends are connected by a suture material offset from the central longitudinal axis thereof. Due to the parallel over-under orientation of the firing mechanism and the longitudinally extending fastener magazine, the elongated body portion of the device requires a substantial cross-sectional area and necessarily requires a correspondingly wide distension of the knee joint to access the meniscal tissue to be repaired.

A refinement to the meniscal repair technique is disclosed in commonly assigned co-pending U.S. patent application Ser. No. 09/829,804 (hereinafter "the '804 application), filed Apr. 10, 2001, entitled "Single Shot Meniscal Repair Device", the entire contents of which are hereby incorporated by reference. This application discloses a repair device which incorporates a minimally sized elongate body portion configured to hold a single fastener adjacent a distal end thereof. The elongate body portion is part of a disposable loading unit ("DLU") structure which provides a 360° rotational capability about its longitudinal axis. The elongate body portion includes push rods for expelling a fastener. The elongate body portion may be provided with a locating barb at its distal end to assist in the stabilization of the device at the firing point. The repair device may be provided with a plurality of interchangeable DLU's. One of the DLU's may have a distal portion which is angled off axis to enhance the versatility of the device.

When using a mechanical repair device, such as the device disclosed in the '804 application, the need exists for a series of surgical templates which substantially approximate the configuration of the DLU and the path the DLU will follow through the tissue. In this manner, a surgeon can use the series of surgical templates interchangeably in order to select an appropriate DLU which would most effectively deliver the fastener to the surgical site (i.e., the meniscal tear).

SUMMARY

An instrument kit for performing a repair procedure on a meniscal tear in a knee for use in combination with a meniscal repair device is disclosed. The instrument kit includes at least one template having an elongate body defining X, Y and Z axes. Preferably, the elongate body is adapted for insertion in a knee of the patient to approximate a path to a meniscal tear therewithin. The elongate body has a length along the X-axis sufficient to access the meniscal tear and a reduced profile to facilitate passage thereto. Upon subsequent removal of the template from the knee, a correspondingly dimensioned meniscal repair device is introduced along the path to the meniscal tear for repair thereof. It is envisioned that the elongate body includes an atraumatic tip in order to reduce injury to tissue within the knee.

The elongate body defines a height along the Z-axis and a width along the Y-axis, wherein the width is preferably less than the height. Preferably, the at least one template includes an elongate body having a distal end portion which is obliquely arranged with respect to the X-axis. In one embodiment the distal end portion of the at least one template is offset in a direction of the Y-axis, while in another embodiment the distal end portion is offset in a direction of the Z-axis. It is envisioned that the atraumatic tip of the at least one template includes a distal end surface defining a dimple formed therein.

It is envisioned that the instrument kit may further include a handle configured and adapted to be removably attached to a proximal end of each of the at least one template. It is further envisioned that the handle is either integrally formed with or fixedly secured to a proximal end of the at least one template.

The instrument kit may further include at least one disposable loading unit corresponding in size and shape to the one template. The one disposable loading unit includes an elongate body defining X, Y and Z axes and is adapted to follow the path to the meniscal tear. It is further envisioned that the instrument kit includes a plurality of disposable loading units. A first disposable loading unit includes a substantially linear elongate body, a second disposable loading unit includes a distal end portion which is offset in a direction of the Y-axis and a third disposable loading unit includes a distal end portion which is offset in a direction of the Z-axis.

In an alternative embodiment, the instrument kit includes first and second templates. Each template includes an elongate body defining X, Y and Z axes with each elongate body being adapted for insertion in a knee of the patient in order to approximate a path to a meniscal tear within the knee. Each elongate body has a length along the X-axis sufficient to access the meniscal tear and a reduced profile to facilitate passage thereto. The elongate body of the first template is preferably substantially linear while the elongate body of the second template has a distal end portion which is obliquely arranged with respect to the X-axis. It is contemplated that the distal end portion of the second template is offset in a direction of the Y-axis. The instrument kit further includes a third template having an elongate body defining X, Y and Z axes, wherein the elongate body of the third template is offset in a direction of the Z-axis.

A method of performing a repair procedure or a meniscal repair in a knee is disclosed. The method includes the steps of introducing an elongate template within the knee area of a patient to approximate a path to a meniscal tear within the knee, advancing a repair device along the path to the position adjacent the meniscal tear and actuating the repair device to at least partially repair the meniscal tear. The elongate template may include a substantially straight elongate body or posses a distal portion which is angularly offset relative to a longitudinal axis of the elongate body. Preferably, the elongate template is removed prior to the step of advancing the repair device.

These and other advantages and features of the instrument kit and method, disclosed herein, will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodiments of the disclosure and, together with the general description given above, and the detailed description of the embodiments given below, serve to explain the principles of the present disclosure.

DETAILED DESCRIPTION OF PREFERRED EMBODIMENTS

Figure 1:
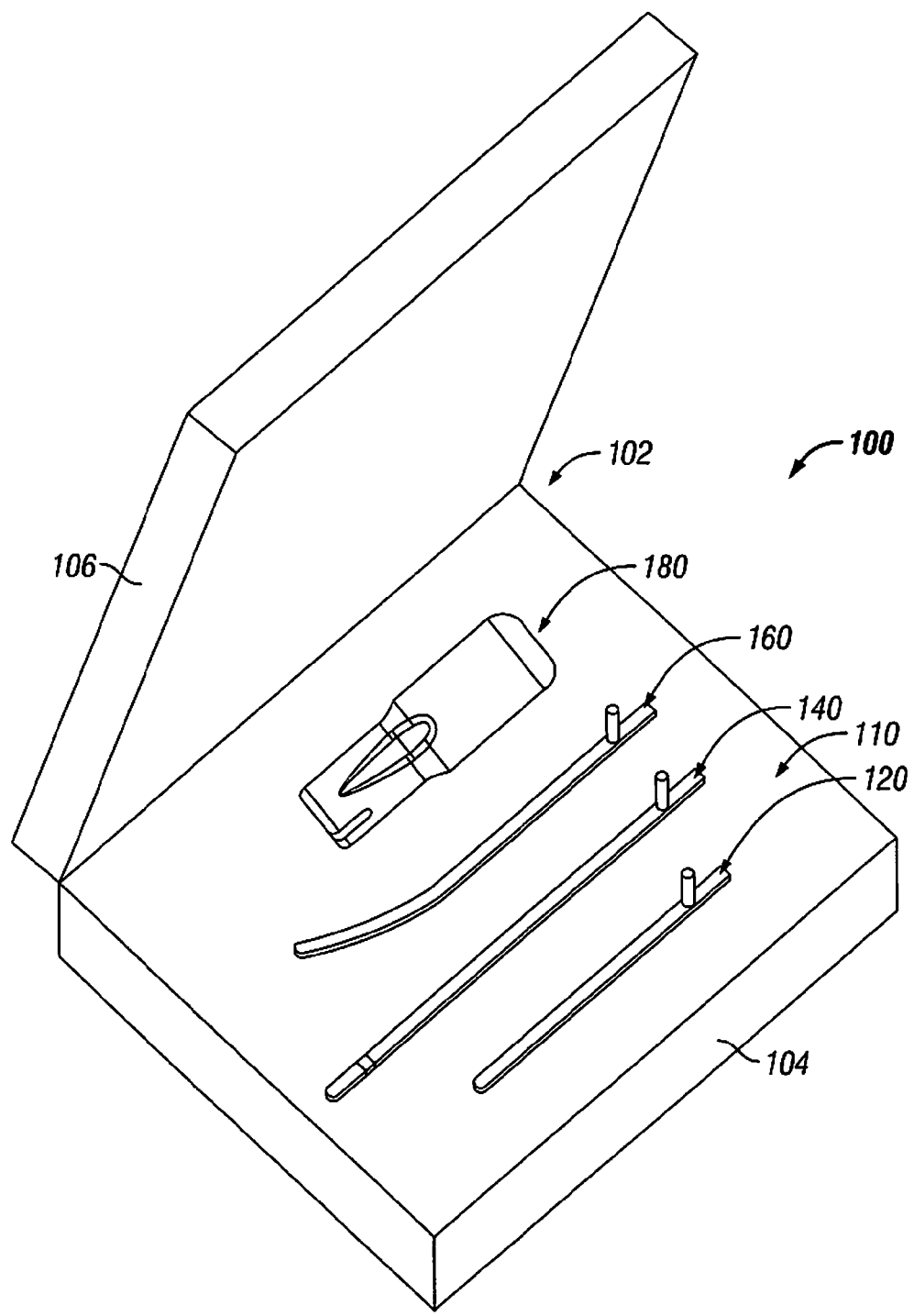
FIG. 1 is a perspective view of the meniscal repair instrument kit in accordance with the present disclosure.

Preferred embodiments of the presently disclosed instrument kit will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Instrument Kit

Referring initially to FIG. 1, an instrument kit for performing a meniscal repair, in accordance with the principles of the present disclosure, is shown generally as reference numeral 100. Instrument kit 100 includes a container 102 for storing the surgical components contained in kit 100. Container 102 includes a bottom portion 104 and a cover portion 106 configured and adapted to enclose the surgical components within container 102. Cover portion 106 is attached to bottom portion 104 along respective peripheral portions via a hinge-like structure, such as, for example, a living hinge. Container 102 may be fabricated from any suitable material including steel, polymeric materials, cardboard, etc. Alternatively, container 102 may be fabricated from an injection molding process as is known in the art.

Templates

Instrument kit 100 includes a set of templates 110 including, but not limited to, a straight template 120, a top-to-bottom angled template 140, a left-to-right angled template 160 and an interchangeable template handle 180.

Figure 2:
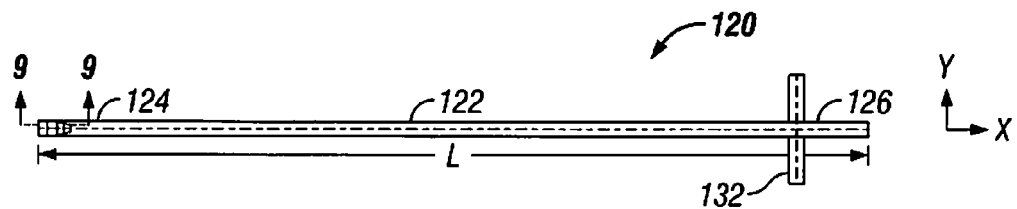
FIG. 2 is a side elevational view of a straight template of the kit of FIG. 1.
Figure 3:
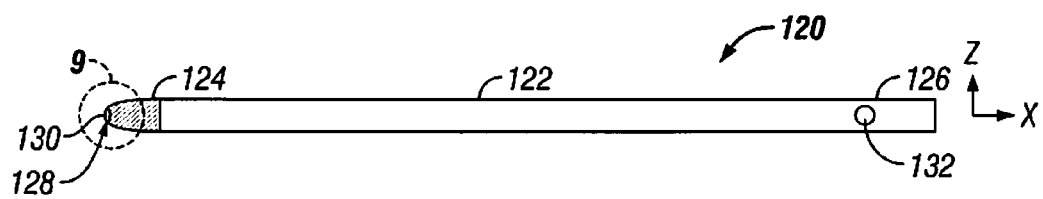
FIG. 3 is a top plan view of the straight template of FIG. 2.
Figure 8:
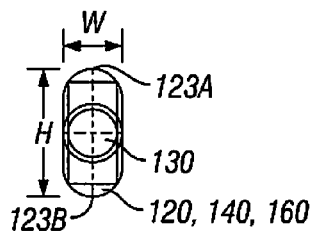
FIG. 8 is an axial end view of the distal end portion of the templates shown in FIGS. 2-7.

As seen in FIGS. 2 and 3, straight template 120 includes an elongate body 122 having a distal end portion 124 and a proximal end portion 126 defining a longitudinal "X" axis. Preferably, elongate body portion 122 is of reduced profile having a length "L" and having a substantially rectangular cross-section defining a height "H" and a width "W" which is less than height "H" (see FIG. 8). Preferably, elongate body portion 122 is provided with arcuate upper and lower surfaces 123A, 123B, respectively. Width "W" defines an axis "Y" while height "H" defines an axis "Z". Preferably, as best seen in FIG. 3, height "H" of distal end portion 124 tapers from the proximal end toward the distal end and defines an atraumatic distal end.

Distal end portion 124 of straight template 120 terminates in a distal terminal end surface 128 having a dimple 130 formed therein. Proximal end portion 126 is provided with a lock rod 132 extending transversely therethrough. Preferably, lock rod 132 is parallel to the "Y" axis.

In accordance with the present disclosure, straight template 120 is preferably dimensioned to have an overall length "L" of between about 5.0 to 7.0 inches, preferably about 5.95 inches, to have an overall height "H" of between about 0.1 to 0.3 inches, preferably about 0.22 inches and to have an overall width "W" of between 0.08 to 0.11 inches, preferably about 0.095 inches. Preferably, lock rod 132 of straight template 120 is positioned approximately 0.5 inches from the proximal most end of body portion 122 and has an overall length of about 0.875 inches. Other dimensions for "L", "H" and "W" are also contemplated.

Figure 4:
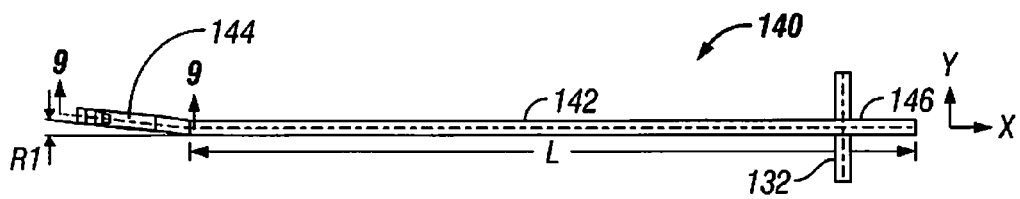
FIG. 4 is a side elevational view of a first angled template of the kit of FIG. 1.
Figure 5:
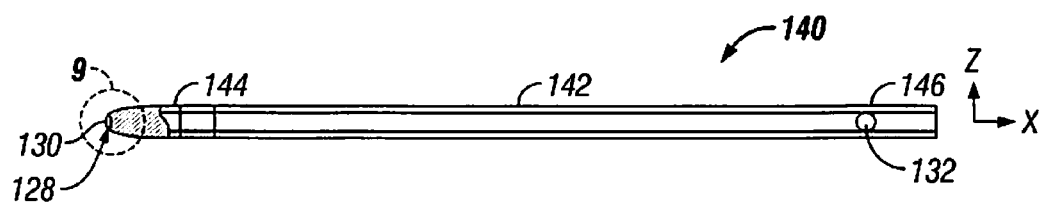
FIG. 5 is a top plan view of the first angled template of FIG. 4.

Turning now to FIGS. 4 and 5, top-to-bottom angled template 140 includes an elongate body 142 having a distal end portion 144 and a proximal end portion 146 defining a longitudinal "X" axis. Preferably, elongate body portion 142 has a length "L", from the proximal most end to a location of where distal end portion 144 begins to angle relative to elongate body portion 142. As best seen in FIG. 4, distal end portion 144 of top-to-bottom angled template 140 is angled in the "Y" direction through an arc "R1" of about 5° to about 15°, preferably about 10°.

In accordance with the present disclosure, top-to-bottom angled template 140 is preferably dimensioned to have a length "L" of between about 5.0 to 6.0 inches, preferably about 5.25 inches, to have an overall height "H" of between about 0.1 to 0.3 inches, preferably about 0.22 inches and to have an overall width "W" of between about 0.08 to 0.11 inches, preferably about 0.095 inches. It is envisioned that other dimensions are also possible.

Figure 6:
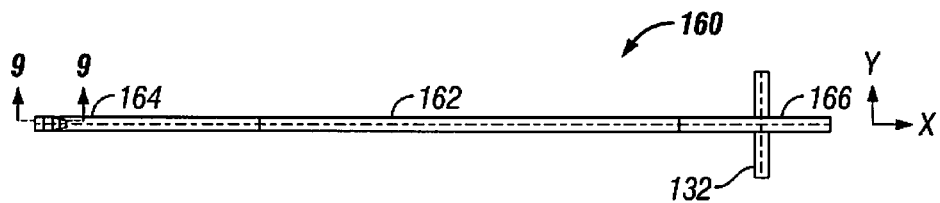
FIG. 6 is a side elevational view of a second angled template of the kit of FIG. 1.
Figure 7:
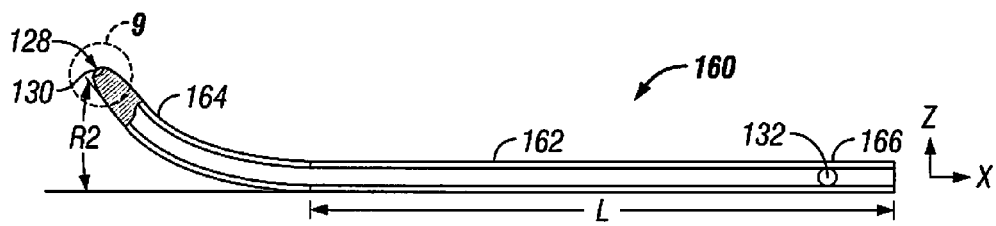
FIG. 7 is a top plan view of the second angled template of FIG. 6.

Turning now to FIGS. 6 and 7, left-to-right angled template 160 includes an elongate body 162 having a distal end portion 164 and a proximal end portion 166 defining a longitudinal "X" axis. Preferably, elongate body portion 162 has a length "L", from the proximal most end to a location of where distal end portion 164 begins to angle relative to elongate body portion 162. As best seen in FIG. 7, distal end portion 164 of left-to-right angled template 160 is angled in the direction of the "Z" axis through an arc "R2" of about 15° to about 45°, preferably about 30°.

Left-to-right angled template 160 is preferably dimensioned to have a length "L" of between about 4.0 to 6.0 inches, preferably about 4.64 inches, to have an overall height "H" of between about 0.1 to 0.3 inches, preferably about 0.22 inches and to have an overall width "W" of between about 0.08 to 0.11 inches, preferably about 0.095 inches.

Figure 9:
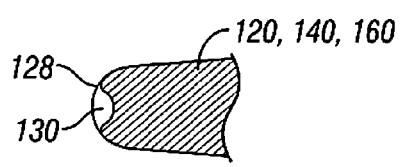
FIG. 9 is an enlarged cross-sectional view of a distal end, indicated by area "9" of FIGS. 3, 5 and 7, taken through "9-9" of the templates of FIGS. 2-7.

As seen in detail in FIG. 9, an enlarged cross-section view of distal end portions 124, 144 and 164 of templates 120, 140 and 160, respectively, is shown. Dimple 130 formed in distal terminal end surfaces 128, 148 and 168 has a diameter of about 0.073 to 0.083 inches and preferably about 0.078 inches.

Figure 10:
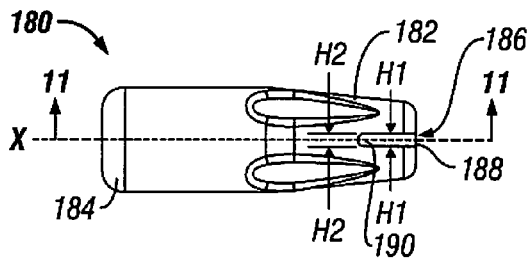
FIG. 10 is a plan view of a template handle of the kit of FIG. 1.
Figure 12:
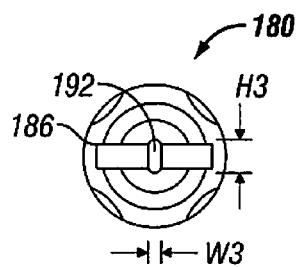
FIG. 12 is a front elevational view of the handle of FIG. 10.
Figure 11:
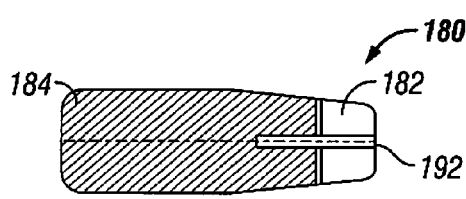
FIG. 11 is a side elevational view, in cross-section, of the template handle of FIG. 10, taken along "11-11"

Turning now to FIGS. 10-12, interchangeable template handle 180 includes a distal end 182 and a proximal end 184 defining a longitudinal "X" axis. Handle 180 includes a groove 186 formed in distal end 182, wherein groove 186 has a depth and extends beyond the radial boundary of handle 180. Groove 186 has a distal portion 188 having a height "H1" and a proximal portion 190 having a height "H2". Handle 180 further includes a bore 192 formed in distal end 182. Bore 192 is aligned with the longitudinal "X" axis and preferably has a depth which is greater than the depth of groove 186. Preferably, bore 192 is substantially rectangular in shape and is orthogonally oriented with respect to groove 186.

Handle 180 can be interchangeably mounted to the proximal end portions 126, 146 and 166 of templates 120, 140 and 160, respectively. As such, height "H1" of distal portion 188 of groove 186 is about 0.121 to about 0.123 inches while height "H2" of proximal portion 190 of groove 186 is about 0.126 to about 0.128 inches. Further, distal portion 188 of groove 186 has a depth of about 0.5 inches and proximal portion 190 of groove 186 has a depth of about 0.064 inches. Further, bore 192 is dimensioned to receive proximal end portions 126, 146 and 166 of templates 120, 140 and 160, respectively, therein. Preferably, as seen in FIGS. 11 and 12, bore 192 has a height "H3" from about 0.226 inches to about 0.23 inches, a width "W3" of about 0.1 inches and a depth "D3" from about 1.12 inches to about 1.13 inches.

Groove 186 and bore 192 of handle 180 permit proximal end portions 126, 146 and 166 of templates 120, 140 and 160, respectively, to be interchangeably mounted thereto. In particular, a snap-fit type coupling exists between handle 180 and templates 120, 140 and 160 in that height "H1" of distal portion 188 of groove 186 is dimensioned to be smaller than lock rod 132 so that lock rod 132 snuggly passes therethrough and height "H2" of proximal portion 190 of groove 186 is dimensioned to be larger than lock rod 132 in order to comfortably receive lock rod 132 therein.

Figure 13:
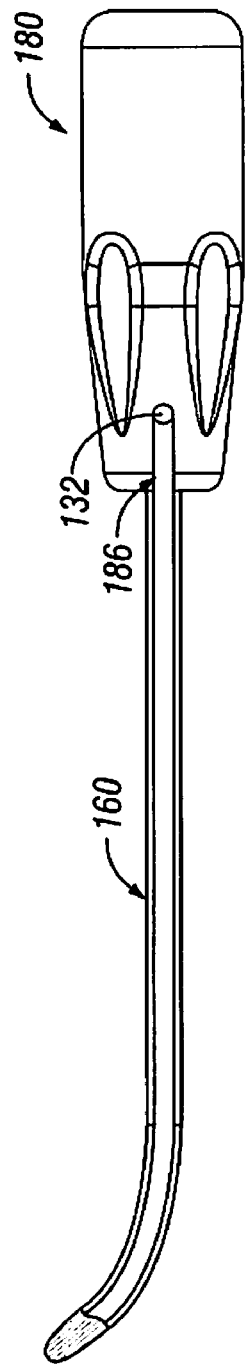
FIG. 13 is a plan view illustrating the attachment of the second angled template of FIG. 7 to the template handle of FIG. 10.
Figure 14:
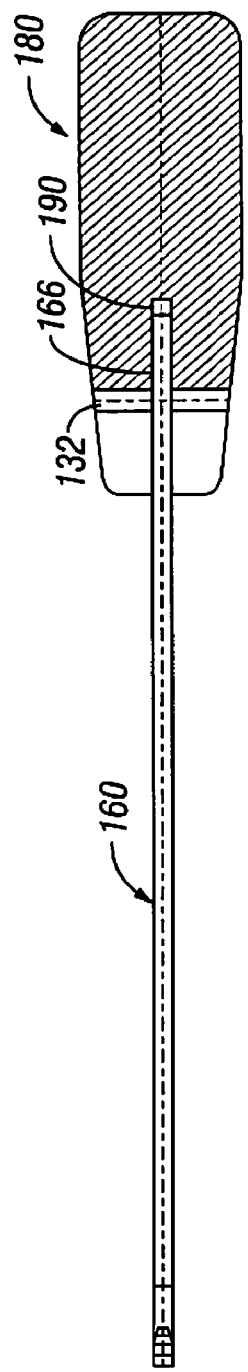
FIG. 14 is a side elevational view, in cross-section, illustrating the attachment of the second angled template of FIG. 7 to the template handle of FIG. 10.
Figure 15:
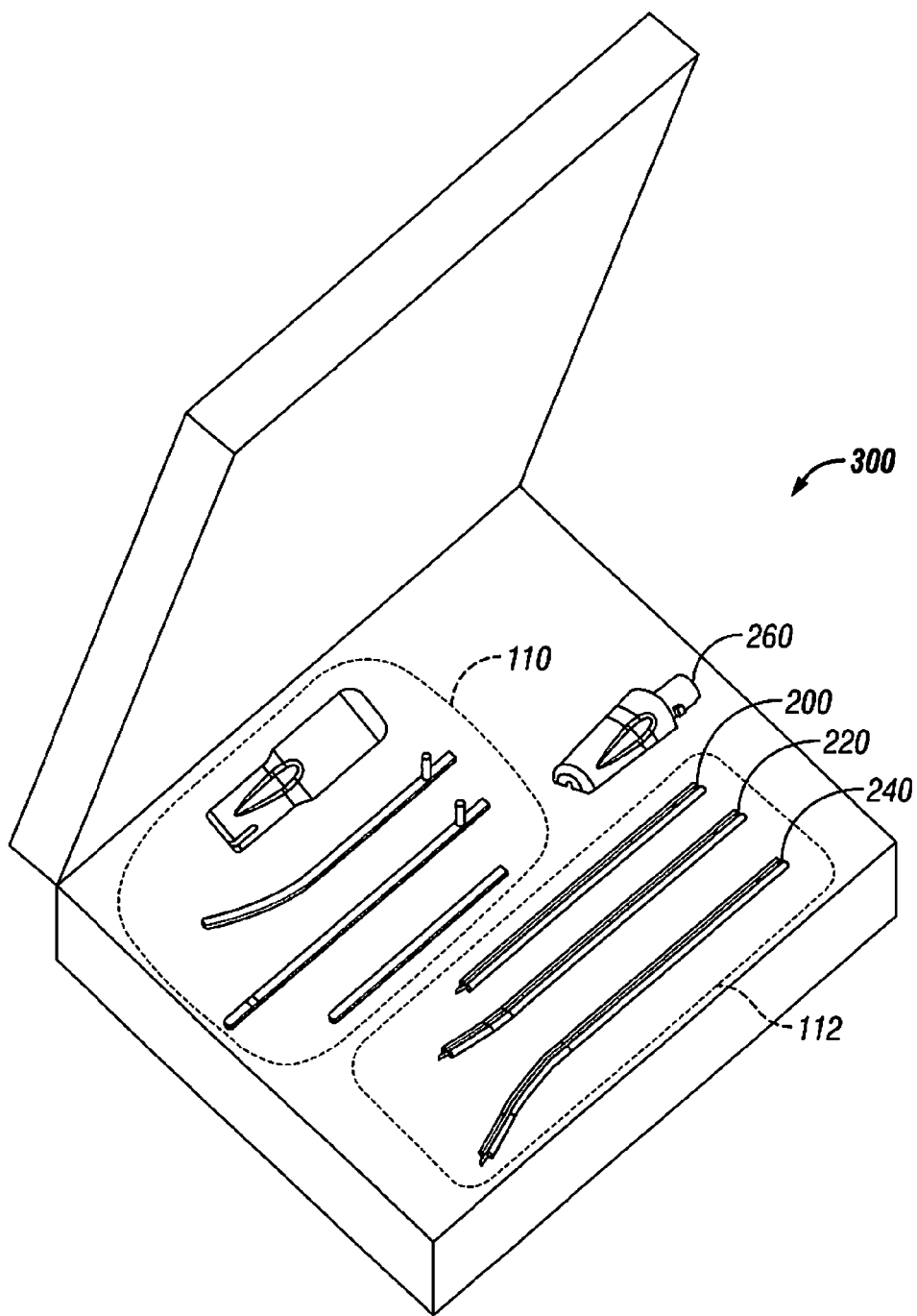
FIG. 15 is a perspective view of the meniscal repair instrument kit in accordance with an alternative embodiment of the present disclosure.

As illustrated in FIGS. 13 and 14, left-to-right angled template 160 is shown removable attached to template handle 180. In particular, proximal end portion 166 of template 160 is inserted into bore 192 (see FIGS. 10-12) of handle 180 such that lock rod 132 enters groove 186 and is snap-fit into proximal portion 190 thereof. While left-to-right angled template 160 is shown attached to template handle 180 it is understood that any of templates 120, 140 and 160 can be removably attached to handle 180 as needed by the surgeon.

While an interchangeable template handle 180 has been shown and described, it is envisioned and within the scope of the present disclosure that each template 120, 140 and 160 include a handle which is integrally formed and/or fixedly attached to the proximal ends thereof. In this manner, the surgeon merely selects the desired template 120, 140 and/or 160 without having to attach a handle thereto.

Instrument Kit Including Mechanical Repair Device

Turning now to FIGS. 15-22, an instrument kit 300 including a set of templates 110 and a set of disposable loading units 112 (hereinafter "DLU's") for a mechanical repair device, in accordance with an alternative embodiment of the present disclosure is shown and described.

Figure 16:
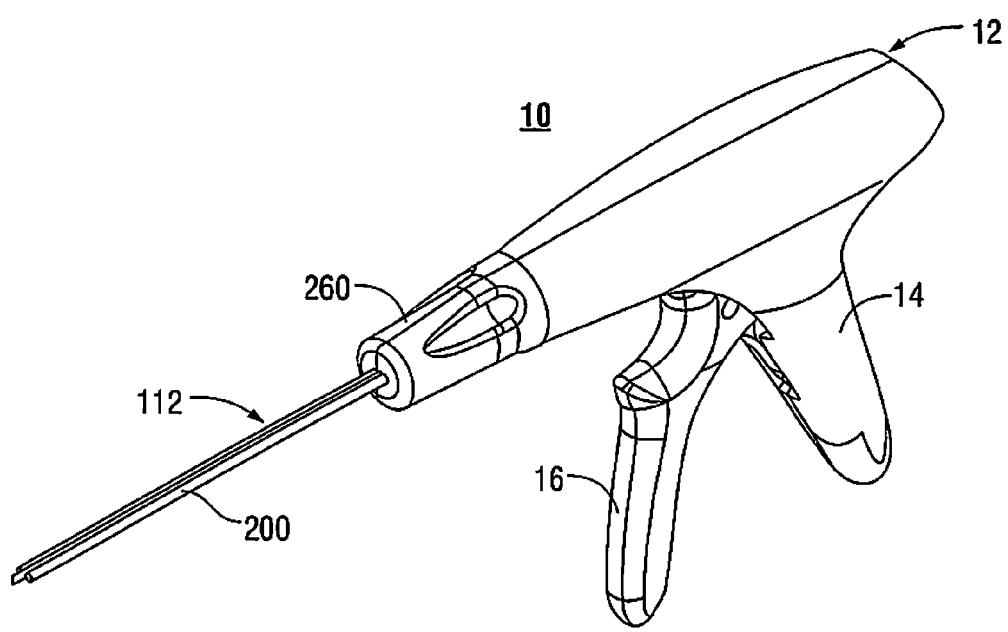
FIG. 16 is a perspective view of a mechanical repair device suitable for use with the templates of the present invention.

Referring initially to FIG. 16, a mechanical repair device, as disclosed in co-pending U.S. patent application Ser. No. 09/829,804, filed Apr. 10, 2001, entitled "Single Shot Meniscal Repair Device", the entire contents of which are incorporated herein by reference, is shown generally as reference numeral 10. It is envisioned that mechanical repair device 10 can be used in cooperation with instrument kit 300 for performing a meniscal repair. Briefly, mechanical repair device 10 includes a handle assembly 12 having a fixed handle portion 14 and a trigger portion 16. Preferably, repair device 10 is configured and adapted to operate in conjunction with disposable loading units 112 of the present disclosure. Repair device 10 is contemplated to be a component of instrument kit 300 of FIG. 15.

The set of DLU's 112 includes a straight removable firing body 200, a top-to-bottom angled removable firing body 220, a left-to-right angled removable firing body 240 and an interchangeable hub 260 for coupling firing bodies 200, 220 and 240 to mechanical repair device 10.

Figure 17:
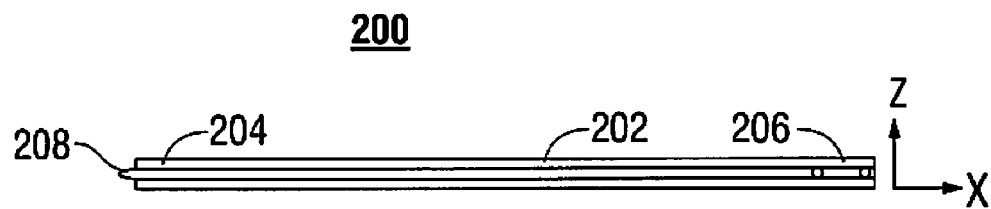
FIG. 17 is a top plan view of a straight removable firing body for the mechanical repair device of FIG. 16 and a component of the kit of FIG. 15.
Figure 18:
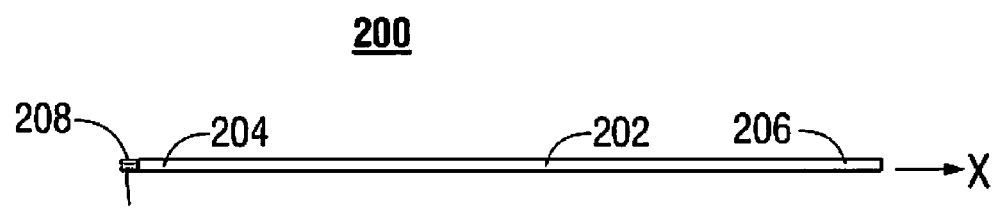
FIG. 18 is a side elevational view of the straight removable firing body of FIG. 17.

As seen in detail in FIGS. 17 and 18, straight removable firing body 200 includes an elongate body 202 having a distal end portion 204 and a proximal end portion 206 defining a longitudinal "X" axis. Elongate body 202 has a width defining a "Z" axis. Straight firing body 200 includes at least one locating barb 208 extending distally from distal end portion 204 in order to assist the stabilizing of firing body 200 at the firing point.

Figure 19:
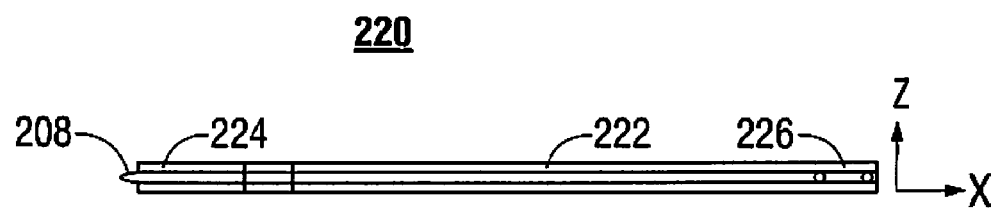
FIG. 19 is a top plan view of a first angled removable firing body for the mechanical repair device of FIG. 16 and a component of the kit of FIG. 15.
Figure 20:
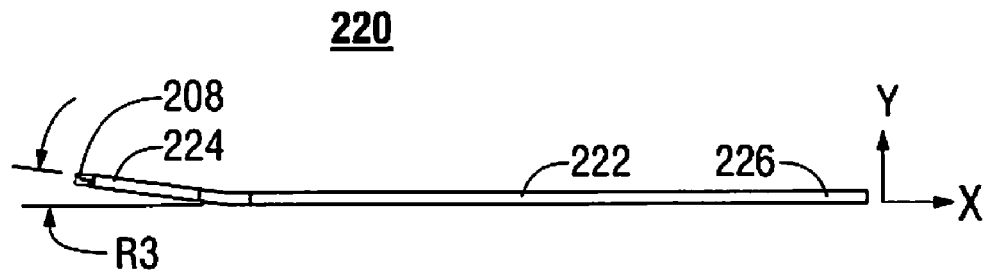
FIG. 20 is a side elevational view of the first angled removable firing body of FIG. 19.

As seen in detail in FIGS. 19 and 20, top-to-bottom angled removable firing body 220 includes an elongate body 222 having a distal end portion 224 and a proximal end portion 226 defining a longitudinal "X" axis. Elongate body 222 has a width defining a "Z" axis. Top-to-bottom firing body 220 is angled an amount "R3" in a "Y" direction which is perpendicular to the "X" and "Z" axes. Preferably, angular amount "R3" of distal end portion 224 is about 5° to about 15°, and more preferably about 10° in a "Y" direction relative to the "X" axis. Top-to-bottom firing body 220 includes at least one locating barb 208 extending distally from distal end portion 224 in order to assist the stabilizing of firing body 220 at the firing point.

Figure 21:
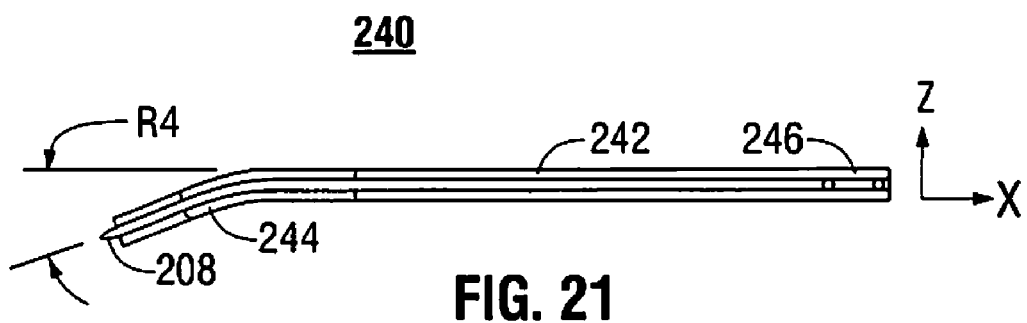
FIG. 21 is a top plan view of a second angled removable firing body for the mechanical repair device of FIG. 16 and a component of the kit of FIG. 15.
Figure 22:
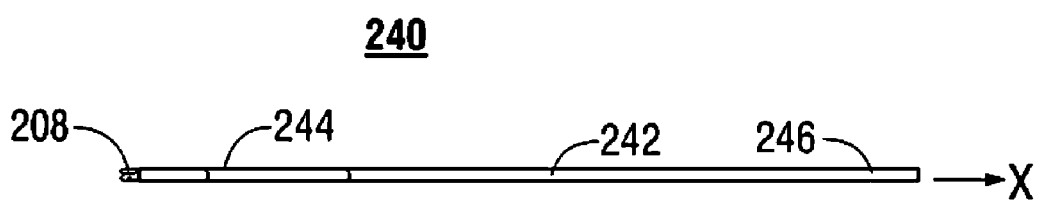
FIG. 22 is a side elevational view of the second angled removable firing body of FIG. 21.

As seen in detail in FIGS. 21 and 22, left-to-right angled removable firing body 240 includes an elongate body 242 having a distal end portion 244 and a proximal end portion 246 defining a longitudinal "X" axis. Elongate body 242 has a width defining a "Z" axis. Left-to-right firing body 240 is angled an amount "R4" in a "Z" direction. Preferably, angular amount "R4" of distal end portion 244 is about 15° to about 45°, and more preferably about 30° in the "Z" direction relative to the "X" axis. Left-to-right firing body 240 includes at least one locating barb 208 extending distally from distal end portion 244 in order to assist the stabilizing of firing body 240 at the firing point.

Straight firing body 200 substantially corresponds is size and shape to straight template 120, top-to-bottom firing body 220 substantially corresponds in size and shape to top-to-bottom template 140 and left-to-right firing body 240 substantially corresponds in size and shape to left-to-right template 160.

Each firing body 200, 220 and 240 includes a pair of push rods (not shown) extending therethrough for expelling a fastener (not shown) out their respective distal ends, across a meniscal tear, in order to facilitate the healing of the meniscal tear. Firing bodies 200, 220 and 240 are configured and angled in such a manner, as described above, that the surgeon performing the meniscal repair procedure can select a particular one of the firing bodies which would best drive a fastener across the meniscal tear. The selection of the appropriate firing body to use in a particular meniscal repair procedure is an iterative process in which the surgeon inserts the various firing bodies into the target site until, through trial and error, the surgeon is satisfied with the positioning of the distal end of the selected firing body. Locating barbs 208 ensure that the distal end of the selected firing body is stabilized and properly positioned with respect to the meniscal tear. Accordingly, the surgeon presses the selected firing body against the target site thus pressing locating barb 208 into the meniscal tear.

Use of Instrument Kit

Figure 23:
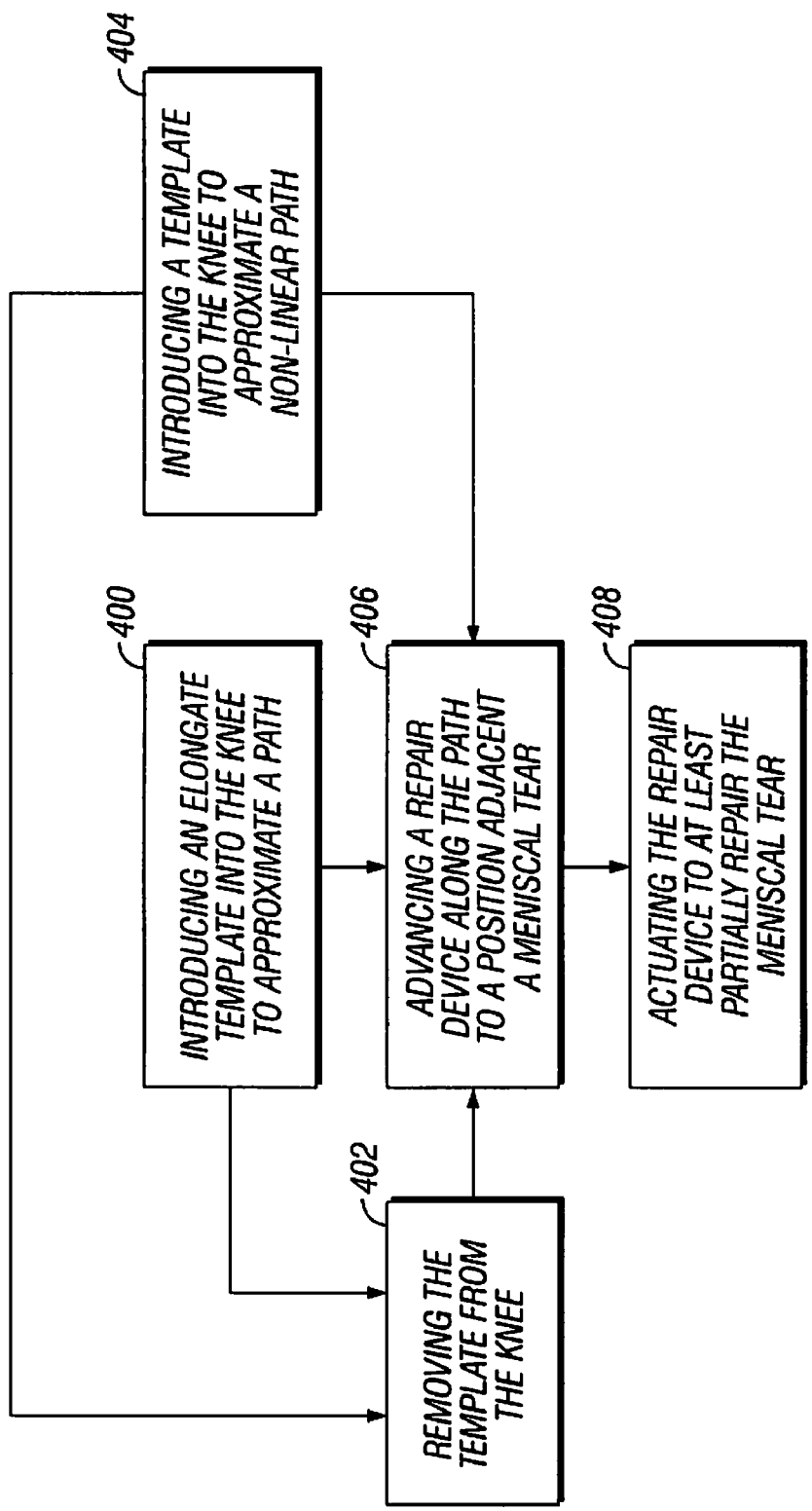
FIG. 23 is a flow chart illustrating a method of performing a meniscal repair procedure using the instrument kit of FIG. 1.

With reference to FIG. 23, a preferred method of use and operation of instrument kits 100 and 300, for performing a meniscal repair, will now be described in greater detail. The surgeon makes an incision in the knee and then proceeds to select a first template 120, 140 or 160, from the set of templates 110. The surgeon then inserts the first selected template 120, 140 or 160 into the knee to create a first path in which the distal end of the first selected template 120, 140 or 160 is positioned against the meniscal tear (Step 400). The first selected template 120, 140 or 160 grossly defines a first path through the knee to the target staple site.

If the surgeon is satisfied with the positioning of the distal end of the first selected template 120, 140 or 160 across the meniscal tear, the surgeon withdraws the first selected template 120, 140 or 160 from the knee and selects a first firing body 200, 220 or 240 from the set of firing bodies 112 which substantially corresponds in size and shape to the first selected template 120, 140 or 160, as described above (Step 402). Alternatively, a second template may be inserted in the knee to create a path if it is ascertained that the first template fails to access the desired staple site (Step 404). After coupling the first selected firing body 200, 220 or 240 to mechanical repair device 10, the surgeon inserts the first selected firing body 200, 220 or 240 into the knee, along the path created by the first selected template 120, 140 or 160 until the distal end thereof and, more particularly, locating barb 208, contacts the target site (Step 406). The surgeon then stabilizes the distal end of the first selected firing body 200, 220 or 240 in position with respect to the meniscal tear by pressing the first selected firing body 200, 220 or 240, and the attendant locating barb 208, forward to penetrate into the target site.

With the distal end of the first selected firing body 200, 240 or 260 positioned at the target site, such that the body portion of the selected firing body 200, 220 or 240 spans the meniscal tear, the surgeon manipulates mechanical repair device 10 in order to expel and drive the fastener into the meniscus (Step 408). Preferably, as disclosed in co-pending U.S. patent application Ser. No. 09/829,804, the fastener includes a pair of anchor members linked by a flexible member preferably extending between adjacent side surfaces. Preferably, when the surgeon fires mechanical repair device 10, the fastener is driven into the meniscus such that an anchor member is driven into either side of the meniscal tear and the flexible member extends across the tear.

After withdrawing the selected firing body 200, 220 or 240 from the knee the surgeon evaluates whether each anchor member of the fastener has been sufficiently driven into the meniscus. If either of the anchor members has not been sufficiently driven into the meniscus by the mechanical repair device 10, the surgeon reinserts the distal end of the selected template 120, 140 or 160, from above, into the knee such that dimple 130 is seated on the proximal end of the anchor member which is projecting from the meniscus. The surgeon then manually presses or taps the selected template 120, 140 or 160 on the proximal end of the anchor member to further drive the anchor member into the meniscus. It is envisioned that the surgeon can repeat the above steps as many times as necessary in order to repair the meniscal tear.

Figure 24:
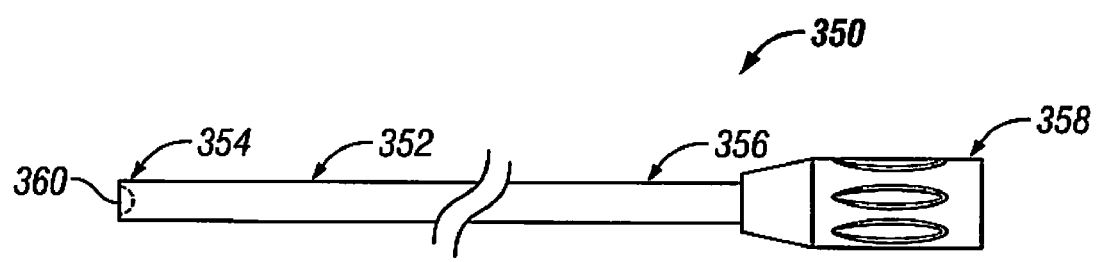
FIG. 24 is a plan view of a driving tool in accordance with the present disclosure.
Figure 25:
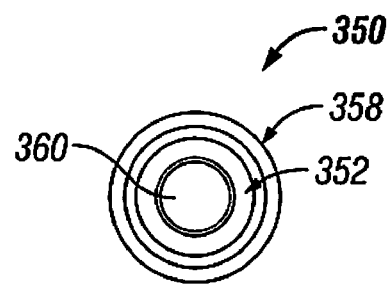
FIG. 25 is side elevational view of the driving tool of FIG. 24 as seen from a distal end thereof.

Alternatively, as seen in FIGS. 24 and 25, instrument kits 100, 300 can be provided with a driving tool in the form of a "pucker stick", generally depicted as 350, to further drive the anchor member into the meniscus. Driving tool 350 includes an elongated body portion 352 having a distal end portion 354 and a proximal end portion 356. Preferably, driving tool 350 includes a handle 358, either fixedly or removably, attached to proximal end portion 356. Driving tool 350 further includes a dimple or recess 360 formed in a distal end surface of distal end portion 354. Dimple 360 is configured and dimensioned to receive the proximal end of an anchor member (not shown). Preferably, driving tool 350 is fabricated from a substantially rigid and inflexible material, such as, for example, stainless steel. As seen in FIG. 25, it is envisioned that driving tool 350 has a uniform circular cross-sectional profile.

It is envisioned that driving tool 350 is used in much the same manner as templates 120, 140 and 160. In particular, if either of the anchor members has not been sufficiently driven into the meniscus by mechanical repair device 10 and templates 120, 140 or 160 are incapable of further driving the anchor member into the meniscus, that the surgeon inserts distal end portion 354 of driving tool 350 into the operative site (i.e., the knee) such that dimple 360 is seated on the proximal end of the anchor member which is projecting from the meniscus. The surgeon then manually presses or taps driving tool 360 into the proximal end of the anchor member to further drive the anchor member in to the meniscus.

Since the distal end of each template 120, 140 and 160 is atraumatically formed the repetitive insertion and withdrawal of templates 120, 140 and 160 into and out of the knee keeps the trauma inflicted in the knee to a minimum.

Thus, the instant disclosure provides an instrument kit and an improved method for performing a meniscal repair procedure. The surgical repair procedure is more efficient and less traumatic to the patient as compared to existing procedures. The instrument kit provides surgical instruments that are specifically adapted for use in the presently disclosed procedure.

While specific embodiments of the present disclosure have been shown and described in detail to show the principles of the present disclosure, it is to be understood that such showing and description have been offered only by way of example and not by way of limitation.

What is claimed is:

1. A method of performing a repair procedure on a patient's knee, comprising the steps of:
   introducing at least one template into the patient's knee to define a path to a tissue site;
   advancing a repair device along the path to position the repair device adjacent the tissue site within the patient's knee;
   actuating the repair device to treat the tissue site; and
   releasably connecting a handle to the at least one template for manipulating the at least one template by connecting receiving structure provided at a distal end of the handle to attachment structure provided at a proximal end of the at least one template, wherein the receiving structure corresponds in configuration and dimensions to the attachment structure to allow application of a proximally directed longitudinal force to the at least one template to access the tissue site, and a distally directed longitudinal force to remove the at least one template from the tissue site.

2. The method of claim 1, wherein the step of advancing a repair device includes providing a repair device corresponding in configuration and dimensions to the introduced template for atraumatically moving the repair device along the path created thereby.

3. The method of claim 1, wherein the step of introducing at least one template includes providing at least one template with an elongate body defining X, Y and Z axes and a reduced profile for facilitating passage to the tissue site.

4. The method according to claim 1 further including the step of creating an opening in the patient's knee for allowing introduction of the at least one template.

5. The method according to claim 1, wherein the step of introducing at least one template includes introducing a first template with a first configuration for initially defining a first path, and introducing a second template with a second, different configuration along the first path to define a second, different path.

\* \* \* \* \*